United States Patent [19]

Weng et al.

[11] Patent Number: 4,737,456

[45] Date of Patent: Apr. 12, 1988

[54] REDUCING INTERFERENCE IN LIGAND-RECEPTOR BINDING ASSAYS

[75] Inventors: Litai Weng, Mountain View; Iam Gibbons, Menlo Park, both of Calif.

[73] Assignee: Syntex (U.S.A.) Inc., Palo Alto, Calif.

[21] Appl. No.: 732,471

[22] Filed: May 9, 1985

[51] Int. Cl.$^4$ ............................................. G01N 33/53
[52] U.S. Cl. ............................................. 435/7; 435/4; 435/810; 436/518; 436/537; 436/547; 436/548; 436/808; 436/817; 436/818; 436/819; 436/825; 935/108; 935/110
[58] Field of Search ............... 435/4, 7, 810; 436/518, 436/537, 547, 548, 808, 817, 818, 819, 825; 935/108, 110

[56] References Cited

U.S. PATENT DOCUMENTS 3,935,074  1/1976  Rubenstein .......................... 436/537
4,376,110  3/1983  David ..................................... 435/7

OTHER PUBLICATIONS

Wada Clinical Chemistry 28(9), pp. 1862–1866 (1982).

Primary Examiner—Robert J. Warden
Assistant Examiner—Robert Benson
Attorney, Agent, or Firm—Theodore J. Leitereg

[57] ABSTRACT

A method for assaying for a ligand analyte which is a member of a specific binding pair ("sbp member") consisting of ligand and its complementary receptor is disclosed. The ligand analyte has a binding site in common with an interfering substance present in a sample suspected of containing the analyte. The interfering substance has at least two binding sites. The method comprises combining in an assay medium without intervening separation (1) the sample, (2) a blocking receptor which does not bind to the ligand and does bind to the interfering substance, thereby blocking the binding of a common receptor to the interfering substance, and (3) a common receptor which binds to the common binding site. Any additional members of a signal producing system capable of producing a detectable signal in relation to the amount of analyte in the sample are added to the assay medium. Next, the assay medium is examined for the presence of a detectable signal. The method has application to both heterogeneous and homogeneous assays.

36 Claims, No Drawings

REDUCING INTERFERENCE IN LIGAND-RECEPTOR BINDING ASSAYS

BACKGROUND OF THE INVENTION

1. Field of the Invention

This invention relates to ligand-receptor binding assay techniques. The determination of the presence or concentration of a ligand analyte which is a member of a specific binding paai ("sbp member") consisting of ligand and its complementary receptor, in serum or other body fluids relies increasingly upon specific binding assay techniques. These techniques are based upon formation of a complex between sbp members in which one or the other member of the complex may be labeled. In the case of a competitive specific binding assay technique, analyte in a sample of fluid being tested for its presence competes with a known quantity of labeled analyte in binding to a limited amount of a complementary sbp member. Thus, the amount of labeled analyte bound to the sbp member varies inversely with the amount of analyte in the sample. In immunometric assays, the analyte is usually a ligand and the assay employes a complementary sbp member and a second labeled receptor, usually an antibody. In such an assay, the amount of labeled receptor associated with the complex is directly related to the amount of analyte substance in the fluid sample.

The presence in the sample of an interfering substance that binds to a receptor being employed to bind with the analyte in question can be a serious factor in comprising the quantitative character of a ligand-receptor assay. The analyte is usually present in very small amounts. The interfering substance, which may be present in greater amounts, can bind to a significant number of receptor molecules and, thus, reduce assay sensitivity. In many situations, the amount of interfering substance will vary from sample to sample thereby preventing accurate reference to a standard or calibrator normally employed to provide for translating the observed signal into the concentration of the analyte. In order to enhance the accuracy of the assay, it is desirable to diminish or completely remove the contribution of the interfering substance to the observed signal.

2. Description of the Prior Art

U.S. Pat. No. 4,362,531 discloses agglutination immunoassays carried out with an agent to reduce non-specific interferences. An improved immunoassay sample determination process for determining the presence of a component of an antigen-antibody reaction in a sample, which process substantially eliminates nonspecific interactions between the sample and the reaction vessel wall surfaces during the antigen-antibody reaction is disclosed in U.S. Pat. No. 4,414,324. U.S. Pat. No. 4,455,381 teaches an immunoassay method for proteins wherein the interference in the assay can be avoided by subjecting the fluid to protein-digestion, using for example an enzyme such as pepsin. A receptor steric hindrance immunoassay for receptor determination is disclosed in U.S. Pat. No. 4,130,462. U.S. Pat. No. 4,233,402 teaches reagents and method employing channeling.

SUMMARY OF THE INVENTION

The present invention is directed to a method for assaying for a ligand analyte which is a member of a specific binding pair ("sbp member ") consisting of the ligand and its complimentary receptor. The ligand analyte has a binding site in common with an interfering substance present in a sample suspected of containing the analyte. The interfering substance has at least two binding sites. The method comprises combining in an assay medium without intervening separation (1) the sample, (2) a blocking receptor which does not bind to the ligand and does bind to the interfering substance, thereby blocking the binding of a common receptor to the interfering substance, and (3) a common receptor which binds to the common binding site. A signal producing system is also employed, which system is capable of producing a detectable signal in relation to the amount of the analyte in the sample. The common receptor can be a member of the signal producing system by virtue of being bound to or part of a label. Any additional signal producing system members are added to the assay medium which is then examined for the presence of a detectable signal. The method has application to both heterogeneous assays wherein a separation step is employed and in homogeneous assays which do not include a separation step. By employing the present method an analyte present in a sample can be accurately quantitated even in the presence of a higher concentration of an interfering substance.

DESCRIPTION OF THE SPECIFIC EMBODIMENTS

Before proceeding further with the description of the specific embodiments of the present invention, a number of terms will be defined.

Analyte—the compound or composition to be measured, which is a member of a specific binding pair and may be a ligand, which is mono- or polyvalent, usually antigenic or haptenic, or a single compound or plurality of compounds which share at least one common epitopic or determinant site.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of the analytes together with numerous examples thereof are disclosed in U.S. Pat. No. 4,299,916 to Litman, et al, particularly columns 16 to 23, the disclosure of which is incorporated herein by reference.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair, although other specific binding pairs such as biotin-avidin, hormones-hormone receptors, nucleic acid duplexes and the like are not immunological pairs.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate may bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Support—a porous or non-porous water insoluble material. The support can be hydrophilic or capable of being rendered hydrophilic and includes inorganic powders such as silica, magnesium sulfate, and alumina; natural polymeric materials, patricularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass, ceramics, metals, and the like.

Binding of sbp members to the support may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

Labeled-sbp member—a label, for example, a catalyst, radioisotope or fluorescent molecule, conjugated to or incorporated in an sbp member, which is a member of the signal producing system. The sbp member can bind directly to the analyte or can bind indirectly to the analyte by binding to an sbp member complementary to the analyte.

Label—A member of the signal producing system that is conjugated to or incorporated in an sbp member. The label may be isotopic or nonistopic, preferably nonisotopic.

Signal Producing System—The signal producing system may have one or more components, at least one component being the label conjugated to an sbp member. The signal producing system includes all of the reagents required to produce a measurable signal. When the label is not conjugated to an analyte analog or a receptor complementary to the analyte, the label is normally bound to an sbp member complementary to the receptor. Other components of the signal producing system may be included in a developer solution and may include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with the enzymic products, other enzymes and catalysts, and the like. The signal producing system provides a signal detectable by external means, normally by measurement of electromagnetic radiation, desirably by visual examination. For the most part, the signal producing system involves a radioactive substance or a chromophoric substrate and enzyme, where chromophoric substrates are enzymatically converted to dyes which absorb light in the ultraviolet or visible region, phosphors or fluorescers or chemiluminescers.

The signal-producing system cna include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

The signal producing system provides for the production of a compound, which is normally the signal generating compound, but in some instances may react with another compound bound to a surface with the production, enhancement or destruction of the signal generating compound. While both enzymatic and nonenzymatic catalysts may be employed, usually when a catalyst is employed there will be at least one enzyme employed in the signal producing system. In the event of there being only one catalyst, this catalyst will usually be conjugated to an sbp member for binding through sbp member complex formation. In addition to the catalyst, there must be a substrate which undergoes a transformation which results in a change in a detectable signal at the measurement surface. For the most part, the product resulting from the transformation catalyzed by the labeled sbp member will be the signal generating compound.

In order to have a detectable signal, it is desirable to provide means for amplifying the signal produced by the presence of the label. Therefore, it will usually be preferable for the label to be a catalyst or luminescent compound or radioisotope, most preferably a catalyst. Preferably catalysts are enzymes and coenzymes which can produce a multiplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Ancillary Materials—Various ancillary materials will frequently be employed in the assay in accordance with the present invention. For example, buffers will normally be present in the assay medium, as well as stabilizers for the assay medium and the assay components. Frequenctly, in addition to these additives, additional proteins may be included, such as albumins, or surfactants, particularly non-ionic surfactants, binding enhancers, e.g., polyalkylene glycols, or the like.

Interfering substance—a substance present in a sample to be assayed for the presence of an analye. The substance is interfering in the sense that the substance specifically binds to a reagent employed in the assay, which reagent is determinative of the amount of analyte in the sample. The interfering substance generally has a binding site in common with the analyte and thus competes for binding sites on a complementary sbp member. Illustrative of such interfering substances are proteins, for example, human chorionic gonadotropin which shares a binding site, namely the $\alpha$-subunit, in common with human thyroid stimulating hormone, human leutinizing hormone, and human follicle stimulating hormone, and drugs such as tobramycin which shares a common binding site with kanamycin, namely the kanasamin aminoglycoside side chain, and so forth.

Blocking receptor—a receptor that binds to the interfering substance and thereby blocks a common receptor from binding to the interferring substance, but does not bind to the ligand analyte. The blocking receptor can be an antibody, preferably a monoclonal antibody.

Common receptor—a receptor capable of binding to a binding site that is common to the analyte of interest and the interfering substance. The common receptor can be, for exmaple, an antibody.

As mentioned above the present method is suitable for assaying for a ligand analyte which is an sbp member. The ligand analyte has a binding site in common with an interfering substance present in the sample suspected of containing the analyte. The interfering substance has at least two binding sites. The method comprises combining in an aqueous medium without intervening separation (1) the sample, (2) a blocking receptor which does not bind to the ligand and does bind to the interfering substance, thereby blocking the binding of a common receptor to the interfering substance, and (3) a common receptor which binds to the common binding site. The common receptor or an analyte analog can contain or be bound to a member of a signal producing system capable of producing a detectable signal in relation to the amount of analyte in the sample by virtue of containing a label. Any required additional members of the signal producing system are added to the assay medium which is then examined for the presence of a detectable signal.

In carrying out the assay an aqueous medium will normally be employed. Other polar solvents may also be employed, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.4–9.5. The pH is chosen so as to maintain a significant level of specific binding by the receptor while optimizing signal producing proficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay and usually constant temperatures during the period of the assay. The temperatures for the determination will generally range from about 10°–50° C., more usually from about 15°–40° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique, and the concentration of the analyte of interest will normally determine the concentration of the other reagents.

While the concentrations of the various reagents will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on binding sites of the analyte and not more than about 10,000 times the maximum concentration of interest based on analyte binding sites, usually about 0.1–1000 times, more usually about 0.3–10 times, the maximum concentration of interest. For ligand analyte, where labelled ligand is employed, the concentration range of the labelled ligand based on equivalents will generally be not less than about $10^{-6}$, more usually not less than $10^{-2}$ times the minimum concentration of interest and not greater than 100, usually not greater than 10, times the maximum concentration of interest.

The concentration of the blocking receptor in the assay medium can vary widely and is preferably present in an excess amount. The blocking receptor should be present at least in an amount equivalent to the maximum suspected amount of interfering substance in the sample. Normally, the blocking receptor will be present in the assay medium in a concentration about $10^{-11}$ to $10^{-4}$M, preferably about $10^{-9}$ to $10^{-6}$M.

The order of addition of the various reagents may vary. Normally, the blocking receptor will be combined with the sample prior to contacting the solution with the second receptor. However, simultaneous addition of the blocking and common receptors may be employed particularly where there is an excess of blocking receptor. Inverse addition of reagents will usually necessitate lengthy incubation times and will be useful where the time required for the assay is not important.

The present invention has particular application to the determination of polyvalent ligand analytes, for example, proteins. However, the present method can also be employed for the determination of monovalent ligands.

As mentioned above the present assay method has application both to heterogeneous and homogeneous assays. Exemplary of heterogeneous assays are the radioimmunoassay (RIA, Yalow and Berson, *J. Clin. Invest.* (1960) 39, 1157), and enzyme linked immunoassays such as the enzyme linked immunosorbant assay (ELISA, "Enzyme-Immunoassay" by Edward T. Maggio, CRC Press Incorporated, Boca Raton, Fla., 1980). Homogeneous immunoassays are exemplified by immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, supra, and in U.S. Pat. No. 3,817,837.

The invention will next be described in more detail with reference to the determination of human thyroid stimulating hormone (hTSH) in a sample suspected of containing hTSH. The sample also contains human chorionic gonadotropin (hCG) as an interfering substance. hTSH and hCG have the same α subunit but have different β subunits. hCG interferes in the hTSH assay by competing with hTSH for binding sites on anti-hTSH antibodies capable of binding to the α subunit. The assay can be performed, for example, by an enzyme channeling technique such as that disclosed in U.S. Pat. No. 4,233,402, the disclosure of which is incorporated herein by reference. In the assay a pair of enzyme antibody conjugates using different enzymes can be employed which are brought together by the analyte. The antibodies in the two conjugates will bind to different sites on hTSH to form a termolecular complex or may bind to the same site provided that a poly hTSH-analog is included. Alternatively, a hTSH-enzyme conjugate and an enzyme antibody conjugate pair can be employed where the hTSH and the hTSH-enzyme conjugate compete for binding to the enzyme antibody conjugate. The sample containing the analyte can therefore be added to a medium containing one member of a conjugate pair, followed by addition of the other member, or the three materials can be added simultaneously. In accordance with the present invention, when an antibody conjugate is able to bind to the α subunit, hCG can be prevented from interferring with accurate quantitation by adding a receptor which does not bind to hTSH but binds only to hCG and blocks binding of the anti-α subunit antibody to the hCG. Additionally, other members of a signal producing system would be added and the medium would be examined for the presence of a detectable signal in relation to the amount of analyte in the sample.

If a heterogeneous immunometric approach is employed, three receptors can be used in accordance with the present method. An antibody specific for hTSH would be bound to a support and the support combined with an aqueous medium containing the sample, a blocking receptor for example, a monoclonal antibody, which does not bind to the hTSH and does bind to the hCG, and an antibody to the common α-subunit binding site of hTSH and hCG labeled with a radioisotope, enzyme, etc. Alternately, an antibody to the common α-subunit binding site of hTSH and hCG could be bound to a support. An antibody specific for hTSH and labeled with a radioisotope, enzyme, etc. is combined with the support in an aqueous medium containing the sample and the blocking receptor. After the above combination is made, the support is removed from the aqueous medium, washed to remove unbound materials, and examined for the presence of a detectable signal produced by the label in relation to the amount of analyte in the sample. Alternatively, the assay medium which has been separated from the support may be examined for the presence of a detectable signal which also relates to the amount of analyte in the sample.

The invention also includes compositions for use in the method for assaying for the presence or amount of an analyte in a sample wherein the analyte is mono, di-, or polyvalent and the sample may contain an interfering substance having at least two binding sites, one of which is common to a binding site on the analyte. The composition comprises, in combination with (1) a common receptor recognizing the common binding site of the ligand analyte and the interfering substance and (2) one or more members of a signal producing system capable of producing a detectable signal in the presence of the analyte, a blocking receptor which does not bind to the analyte and does bind to the interfering substance and thereby blocks the binding between the common receptor and the interfering substance. The composition may additionally include a third receptor specific for the non-common binding site on the ligand analyte.

As a matter of convenience, the reagents employed in the present invention can be provided in a kit in packaged combination with predetermined amounts of reagents for use in assaying for an analyte in a sample. Where an enzyme is used as the label, the reagents will include an enzyme labeled sbp member, substrate for the enzyme, or precursors therefor, including any additional substrates, enzymes and cofactors and any reaction partner of the enzymic product required to provide the detectable chromophore or fluorophore, a blocking receptor for the interfering substance in the sample, and any other members of a signal producing system. In addition, other additives such as ancillary reagents may be included, for example, stabilizers, buffers, and the like. The relative amounts of the various reagents may be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay.

EXAMPLES

The invention is demonstrated further by the following illustrative examples. The following abbreviations are employed.

| | | |
|---|---|---|
| hCG | Human Chorionic Gonadotropin | |
| hTSH | Human Thyroid-Stimulating Hormone | |
| hCGα | α-subunit of hCG | |
| hCGβ | β-subunit of hCG | |
| McAb | Monoclonal Antibody | |
| Tc | Total counts | |
| % B | Percent bound | |
| PBS | Phosphate Buffered Saline: 10 mM sodium phosphate + 150 mM NaCl, pH 7.4 | |
| Buffer A | PBS containing 0.1% BSA and 0.05% Tween 20, pH 7.4 | |
| DMF | Dimethylformamide | |
| SAMSA | S—acetyl mercaptosuccinic anhydride | |
| SMCC | Succinimidyl 4-(N—maleimido methyl)cyclohexane-l-carboxylate | |
| HRP | Horseradish peroxidase | |
| AP | Alkaline Phosphotase | |
| TMB | Tetramethylbenzidine | |
| PVC | Polyvinylchloride | |
| h | hour | |
| r.t. | room temperature | |
| $I^{125}$-hCG | $I^{125}$ labelled hCG | (purchased from Cambridge Medical Diagnostics, Inc.) |
| $I^{125}$-hTSH | $I^{125}$ labelled hTSH | |

The monoclonal antibodies employed in the examples may be produced according to the standard techniques of Köhler and Milstein, (*Nature* (1975) 265:456–497) for producing monoclonal antibodies.

The monoclonal antibodies employed in the following examples were:

McAbhCGα (TSHα)—monoclonal antibody having a binding affinity for the α subunit of hCG and hTSH and designated 9D7.

McAbhCG—monoclonal antibody having a binding affinity for hCG, reacting specifically with native hCG and not with the purified subunits of hCG, designated 1A7.

McAbhTSHβ—monoclonal antibody having specific binding affinity for hTSH and hTSHβ with insignificant cross-reaction with hCG, designated 9G3.

McAbhCG, 1A7, that blocks the binding of hCG to 9D7 on the solid phase was selected by solid phase RIA techniques.

EXAMPLE 1

The wells of Immulon® 2 Removawell® strips were coated with 200 μl (2 μg) of 9D7 in PBS, pH 7.4, at r.t., overnight.

Any unbound antibody on the wells was removed by washing twice with Buffer A, pH 7.4. The wells were then incubated with Buffer A for 2 h at r.t. to saturate any remaining protein binding sites. After 2 h, the buffer was removed from the wells.

Then, 100 μl (0.1ng) $I^{125}$—hTSH with and without (±) hCG (2 μg) in Buffer A was added to each well followed by 100 μl of Buffer A or of Buffer A containing 10 μg 1A7. The mixture was incubated at r.t. with shaking for 2 h.

The wells were washed 3 times with Buffer A. Each well was then read with a γ-counter.

The results are summarized below in Table 1.

TABLE 1

| Conditions 1A7(~10 μg) | hCG(~2 μg) | % B(hTSH) |
|---|---|---|
| − | − | 46 |
| − | + | 1 |
| + | − | 47 |
| + | + | 42 |

The above results indicate that, when a high concentration of hCG was present in the hTSH sample, binding of hTSH to 9D7 bound to the surface was largely inhibited by the interference of hCG. However, this interference was reduced by about 90% in the presence of 1A7.

EXAMPLE 2

The wells of Immulon® 2 Removawell® strips were coated with 200 μl (2 μg) of 9D7 in PBS, pH 7.4 at r.t., overnight.

Any unbound antibody on the wells was removed by washing twice with Buffer A pH 7.4. The wells were then incubated with Buffer A for 2 h at r.t. to saturate any remaining protein binding sites. After 2 h, the buffer was removed from the wells.

Then, 100μl McAbTSHβ—AP (Hybritech Inc.) ± 10 μg 1A7 was added to each well followed by 100 μl hTSH (1ng) ± hCG (2 μg) in Buffer A or 100 μl Buffer A (control). The mixture was incubated with shaking for 2 h. The wells were then washed with Buffer A three times. Following this 200 μl AP substrate, 0.6 mg/ml p-nitrophenyl phosphate in 1M diethanolamine, 1 mM Mgcl₂, pH 9.5, was added.

After 20 minutes, A405 was determined using a microtiter plate reader (Artek Systems Corp. Model 210 Reader, Model 200 Computer).

The results are summarized in Table 2 below.

TABLE 2

| McAbTSHβ-AP ±1A7 (10 μg) | hTSH (1ng) ± hCG (2 μg) | Δ A405 [A405 (sample)- A405 (control)] |
|---|---|---|
| −1A7 | −hCG | 0.733 |
| −1A7 | +hCG | 0.017 |
| +1A7 | −hCG | 0.772 |
| +1A7 | +hCG | 0.718 |

The above results indicate that, when a high concentration of hCG was present in the hTSH sample, binding of hTSH to 9D7 bound to the surface of the wells was largely inhibited by the interference of hCG. This interference was reduced by greater than 90 % in the presence of 1A7.

EXAMPLE 3

PVC sticks (0.6×3 cm) coated with 9D7 (coated 2-sided, 0.6×1 cm) were prepared by immersing PVC sheets (12×3 cm) to a height of 1 cm in a 9D7 solution (~10 μg/ml 9D7 in PBS) and incubating at rt overnight. The sheets were then cut into PVC sticks (0.6×3 cm), and each stick was placed in a croan cup. To this cup was added 0.5 ml McAbTSHβ(9G3)—HRP (containing ~1 μg 9G3, ~1 μg HRP)±1A7 (~100 μg) in Buffer A. The 9G3-HRP conjugate was prepared by the method of Wilson and Nakane, "Immunofluorescence and Related Staining Techniques" (Knapp, W., Holubar, K., & Wick, G., eds.) p. 215–224, Elsevier/North-Holland Biomedical Press, Amsterdam. Next, 0.5 ml hTSH (0.5 ng/ml) ±hCG (20 μg/ml) in Buffer A or Buffer A (for control) was added to the croan cups containing the PVC sticks. The contents of the cups were incubated with shaking for about 1 h. The cups and sticks were washed with Buffer A three times. Next, 1 ml HRP substrate, namely, 0.42 mM TMB plus 1.3 mM $H_2O_2$ in 0.1M sodium acetate, citric acid, pH 6.0 was added. The reaction was stopped by addition of 0.25 ml 2N $H_2SO_4$. After 17 minutes the A450 was determined using a Gilford Stasar III spectrophotometer.

The results are summarized below in Table 3.

TABLE 3

| 4G3-HRP ± 1A7(100 μg) | hTSH (0.25 ng) ± hCG (10 μg) | Δ A450 (17') |
|---|---|---|
| −1A7 | −hCG | 1.78 ± 0.13 |
| −1A7 | +hCG | 0.01 |
| +1A7 | −hCG | 1.58 ± 0.13 |
| +1A7 | +hCG | 1.24 ± 0.02 |

It is evident from the above that 1A7, at the concentration used, reduced the interference of hCG in the hTSH assay by about 70–80%. A higher concentration of 1A7 can be used to achieve a 90–100% reduction in the interference resulting from the presence of hCG in the sample.

The above description demonstrates that an effective assay can be carried out for an analyte in the presence of a large excess of an interfering substance. The assay sensitivity and accuracy is enhanced by employing a compound which blocks the binding of the interfering substance to a common receptor, which binds to the analyte of interest, without blocking the binding of the analyte to the receptor. The present invention, therefore, allows such assay to be conducted on samples containing interfering substances without separation of such substance from the sample prior to conducting the assay. The invention has particular application where prior separation of an interfering substance from the sample is cumbersome, impractical or impossible.

The invention has been described in detail with particular reference to the above embodiments. It will be understood, however, that variations and modifications can be effected within the spirit and scope of the invention.

What is claimed is:

1. A method for assaying for a ligand which is a member of a specific binding pair ("sbp member") consisting of said ligand and its complementary receptor wherein said ligand has a binding site in common with an interfering substance present in a sample suspected of containing said ligand, said interfering substance having at least two binding sites, which method comprises
   combining without intervening separation (1) said sample with (2) a blocking receptor, which does not bind to said ligand and does bind to said interfering substance and thereby blocks binding of a common receptor to said interfering substance, and (3) a common receptor which binds to said common binding site, to provide an assay medium, and determining the extent of binding of said common receptor, the extent of binding being related to the amount of said analyte in said sample.

2. The method of claim 1 wherein said common receptor is an antibody.

3. The method of claim 1 wherein said blocking receptor is a monoclonal antibody.

4. The method of claim 1 wherein said ligand is a protein.

5. The method of claim 1 wherein said blocking and common receptors are antibodies.

6. The method of claim 1 wherein said ligand is human thyroid stimulating hormone (hTSH) and said interfering substance is human chorionic gonadotropin (hCG).

7. The method of claim 6 wherein said common receptor recognizes the alpha sub-unit of hTSH and hCG and said blocking receptor is specific for the beta sub-unit of hCG.

8. The method of claim 1 which is an enzyme linked immunosorbent assay.

9. The method of claim 1 wherein said common receptor is immobilized.

10. The method of claim 1 wherein said common receptor is conjugated to a label.

11. The method of claim 10 wherein said label is an enzyme.

12. The method of claim 10 wherein said label is a radioisotope.

13. The method of claim 10 wherein said label is part of a signal producing system and said determining is carried out by examining said assay medium for the presence of a detectible signal.

14. In an assay method for a ligand which is a member of a specific binding pair ("sbp member") consisting of said ligand and its complementary receptor wherein said ligand has a binding site in common with a binding site of an interfering substance having at least two binding sites, said method employing a receptor recognizing the common binding site, the improvement which comprises adding to an assay medium containing said analyte and said interfering substance, without intervening separation, a specific binding compound which blocks the binding between said receptor and said interfering substance and does not block the binding between said receptor and ligand.

15. The method of claim 14 wherein said receptor is an antibody.

16. The method of claim 14 wherein said receptor is a monoclonal antibody.

17. The method of claim 14 wherein said ligand is a protein.

18. The method of claim 14 wherein said compound is an antibody that binds to said interfering substance.

19. In an assay method for an antigen which is a member of a specific binding pair ("sbp member") consisting of said antigen and its complementary antibody wherein said antigen has at least two epitopic sites, one of said epitopic sites being common to an interfering substance having at least two epitopic sites, said method employing a common antibody, said common antibody recognizing the common epitopic site,
   the improvement which comprises combining with an assay medium containing said antigen and said interfering substance an amount of a blocking antibody sufficient to block the binding between said common antibody and said intefering substance wherein said blocking antibody does not block the binding between said common antibody and said antigen.

20. The method of claim 19 wherein said common antibody is a monoclonal antibody.

21. The method of claim 19 wherein said antigen is a protein.

22. The method of claim 19 wherein said antigen is human thyroid stimulating hormone (hTSH) and said interfering substance is human chorionic gonadotropin (hCG).

23. The method of claim 22 wherein said common antibody recognizes the alph sub-unit of TSH and HCG and said blocking antibody binds only to intact HCG comprised of both the alpha and beta sub-units.

24. The method of claim 19 which is an enzyme linked immunosorbent assay.

25. The method of claim 19 wherein said common antibody is immobilized.

26. In an assay method for a protein analyte having alpha and beta sub-units, wherein one of said sub-units is common to a sub-unit of an interfering protein having alpha and beta sub-units, said method employing a common antibody which recognizes the sub-unit common to said protein analyte and said interfering substance and an antibody specific for the non-common sub-unit of said analyte, the improvement which comprises combinine with said assay medium containing said interfering substance an amount of a blocking antibody that binds specifically to said interfering subtance but not to its separate alpha and beta sub-units, said blocking antibody blocking the binding of said interfering substance to said common antibody.

27. The method of claim 6 wherein said protein analyte is human thyroid stimulating hormone (hTSH) and said interfering substance is human chorionic gonadotropin.

28. A composition comprising one or both of (1) a common receptor that specifically binds to a binding site common to an endogenous interfering substance and a ligand suspected of being present in a sample and (2) members of a signal producing system capable of producing a detectible signal in the presence of said ligand in combination with (3) an amount of a blocking receptor which does not bind to said ligand and does bind to said endogenous interfering substance and thereby blocks the binding between said common receptor and said endogenous interfering substance.

29. The composition of claim 28 wherein said blocking receptor is an antibody.

30. The composition of claim 28 wherein said common receptor is a monoclonal antibody.

31. The composition of claim 28 wherein said ligand is a protein.

32. The composition of claim 28 wherein said blocking and common receptors are antibodies.

33. The composition of claim 28 wherein said ligand is human thyroid stimulating hormone (hTSH) and said interfering substance is human chorionic gonadotropin (hCG).

34. The composition of claim 33 wherein said common receptor recognizes the alpha sub-unit of hTSH and hCG and said blocking receptor binds only to intact hCG comprised of both alpha and beta sub-units of hCG.

35. The composition of claim 28 which additionally comprises a third receptor specific for non-common site on said ligand.

36. A kit for use in an assay method, comprising in packaged combination
the composition of claim 28, and
ancillary reagents as required.

* * * * *